US005468844A

United States Patent [19]

Smith

[11] Patent Number: 5,468,844
[45] Date of Patent: Nov. 21, 1995

[54] PROCESS FOR THE MEMBRANE-FILTERING OF PROTEIN SOLUTIONS

[75] Inventor: Paul Smith, Stirling, Canada

[73] Assignee: Protose Technologies Inc.

[21] Appl. No.: 178,843

[22] Filed: Jan. 7, 1994

[51] Int. Cl.$^6$ .............................. B01D 24/32; C07K 1/34; C07K 14/47; C07K 14/76

[52] U.S. Cl. .................. 530/366; 210/321.68; 210/780; 530/364; 530/386; 530/390.1; 530/414; 530/427; 530/832; 530/833

[58] Field of Search .................... 530/414, 427, 530/390.1, 366, 361, 364, 386, 832, 833; 210/321.67, 321.68, 780

[56] References Cited

U.S. PATENT DOCUMENTS

| | | | |
|---|---|---|---|
| 3,743,480 | 7/1973 | Falk | 530/380 |
| 3,813,289 | 5/1974 | Huber et al. | 530/380 |
| 4,125,527 | 11/1978 | Bahler et al. | 530/366 |
| 4,340,591 | 7/1982 | Lucotte et al. | 530/368 |
| 4,352,695 | 10/1982 | Tomka | 426/576 |
| 4,407,747 | 10/1983 | Lippe et al. | 426/657 |
| 4,462,932 | 7/1984 | Lonergan | 426/657 |
| 4,644,056 | 2/1987 | Kothe et al. | 530/414 |
| 4,721,674 | 1/1988 | Lepienne et al. | 530/368 |
| 4,897,465 | 1/1990 | Cordle et al. | 530/412 |
| 4,906,616 | 3/1990 | Gilchrist et al. | 530/360 |
| 5,008,376 | 4/1991 | Bottomley | 530/366 |
| 5,075,424 | 12/1991 | Tanimoto et al. | 530/361 |
| 5,149,647 | 9/1992 | Burling | 530/366 |
| 5,310,877 | 5/1994 | Spencer | 530/364 |

FOREIGN PATENT DOCUMENTS

| | | | |
|---|---|---|---|
| 591203 | 1/1978 | U.S.S.R. | 210/321.68 |

OTHER PUBLICATIONS

Chemical Engineering, vol. 86, No. 16, issued 1979, pp. 73–76.

Perry et al, Perry's Chemical Engineers Handbook, 6th ed., published 1984 by McGraw–Hill Book Co. (NY), pp. 17–51 through 17–54.

Harris et al, Protein Purification Methods: A Practical Approach, Published 1989 by IRL Press (NY), pp. 80–87.

*Primary Examiner*—Jeffrey E. Russel
*Attorney, Agent, or Firm*—Nath & Associates; Gary M. Nath

[57] ABSTRACT

An improvement is provided in a process for the membrane filtration of a protein solution. The improvement consists of applying a high shear force at the surface of the membrane. In embodiments of such process, the liquid is subjected to membrane filtration utilizing a rotating membrane disc mounted in close proximity e.g., about ⅛" to about ¼" to a stationary solid disc, or a rotating solid disc mounted in close proximity e.g., about ⅛" to about ¼" to a stationary membrane surface with the relative rotation being between bout 1,000 and about 3,450 RPM. This results in permeation characteristics of the selected membrane which essentially represents its theoretical molecular weight cut-off.

12 Claims, No Drawings

PROCESS FOR THE MEMBRANE-FILTERING OF PROTEIN SOLUTIONS

BACKGROUND OF THE INVENTION (i) Field of the Invention

This invention relates to a process for the treatment of protein solutions.

(ii) Description of the Prior Art

Whey proteins are commonly concentrated through the use of ultrafiltration. However, attempts to utilize membranes in processes which require the protein to permeate through the membrane [e.g., microfiltration (MF) for bacterial removal or selective fractionation of proteins by ultrafiltration (UF)] have been less successful. Standard organic membranes in spiral or flat sheet format exhibit soiling which may be partially due to the formation of a secondary membrane layer resulting in the rejection of proteins sized well below the molecular weight cut off (MWCO) for that membrane. For example, beta-lactoglobulin (MW: 18,000) which exists as a dimer in whey (MW: 36,000) exhibits significant rejection on membranes with much higher MWCO including even MF membranes. This fact has been used as the basis for concentrating beta-lactoglobulin relative to alpha-lactalbumin (MW: 14,000) (see U.S. Pat. No. 5,008,374).

The problem of protein rejection can be controlled in tubular membrane systems through the use of inorganic membranes employing high product recirculation rates and mechanisms to minimize transmembrane pressure which may include cocurrent circulation of permeate. This approach is characterized by high capital and operating costs and is limited to microfiltration applications.

SUMMARY OF THE INVENTION

Aims of the Invention

Consequently, since the above-described processes are not completely successful, it is an object of this invention to provide a process for the treatment of proteins involving the use of the full selection of organic and inorganic membranes available and is applicable in both UF and MF.

Another object of this invention is to provide a process for the fractionation of individual proteins in milk generally or in whey protein solutions in particular.

Yet another object of this invention is the provision of a process for the removal of lipids and/or bacteria from milk generally or from whey protein solutions in particular.

Statement of Invention

The present invention is based on the discovery that, by utilizing a system that applies a very high shear force at the surface of the membrane, permeation of protein sizes down to the approximate molecular weight cut-off of the membrane can be achieved. In other words, the present invention provides an improvement in a process for the membrane filtration of a protein solution. Such improvement comprises applying a high shear force at the surface of the membrane.

Thus, the present invention provides a process for the membrane fractionation of protein solutions which comprises applying a high shear force at the surface of the membrane, the high shear force being generated by relative rotation at a speed of between about 1,000 to about 3,450 RPM between a membrane disc and a solid disc spaced in close proximity to one another with a space therebetween of about ⅛" to about ¼"

Other Features of the Invention

The two embodiments of relative rotation, i.e., where the membrane disc is stationary and the solid disc is rotating, and where the membrane disc is rotating and the solid disc is stationary, are included as two features of this invention.

By another feature of the invention, the protein solution is milk whey, concentrated whey or a purified solution of whey proteins. In one variant of such feature, one or more proteins of higher molecular weight are rejected, which lower molecular weight proteins pass through the membranes. By one facet of that feature of the invention, the higher molecular weight proteins are immunoglobulin and/or bovine serum albumin proteins, and the lower molecular weight proteins are beta-lactoglobulin and alpha-lactalbumin, which are allowed to pass into the permeate. By another facet of that feature of the invention the higher molecular weight protein is beta-lactoglobulin, and the lower molecular weight protein is alpha-lactalbumin, which is allowed to pass into the permeate.

In another such feature of the invention, the permeate is subjected to at least one of further concentration and diafiltration steps to produce a milk or whey protein isolate containing greater than 90% protein on a dry basis.

By another feature of the invention, the membrane has a pore size which is selected to remove bacteria but to allow substantially all protein to pass through the membrane.

By a further feature of the invention, the membrane has a pore size which is selected to remove residual lipid material, but to allow substantially all protein to pass through the membrane.

In other facets of these features of the invention, the permeates are further concentrated and dried to produce individual milk or whey protein fractions.

Generalized Description of the Invention

The shear is most effectively applied by spinning a membrane disc at speeds up to about 3450 RPM, but most often between about 1000 and about 1750 RPM. Alternatively, a stationary membrane disc can be used in combination with a solid, rotating disc held in close proximity to the membrane surface at speeds up to about 3450 RPM, but most often between about 1000 and about 1750 RPM.

Accordingly, this invention provides a process for the membrane filtration of protein solutions. Such process uses standard flat sheet membrane materials. The proteins in the solution of sizes down to the approximate molecular weight cut-off of the membrane are able to cross the membrane and may be recovered in the permeate solution without any significant rejection of these proteins.

Description of Preferred Embodiments of the Invention

The following are examples of the present invention.

Example 1

20 L of cooled sweet whey protein concentrate (35%) were recirculated through a spinning disc ultrafiltration unit (known by the trademark SPINTEK™ Systems ST11) at a flow rate of 4 L/m with the temperature maintained at less than 60° F. This unit was equipped with 0.53 square feet of 1,000,000 MWCO PVDF membrane (Advanced Membrane Technologies) and operated at a rotor speed of 1750 RPM. Permeate was recombined with the feed to maintain a constant volume and the test was carried out for a period of 6 hours. Samples were taken for protein analysis every hour and flux measurements were taken throughout the run.

Analysis for bovine serum albumin, alpha-lactalbumin and beta-lactoglobulin revealed no significant rejection over the course of the test. Bacteria removal was shown to be greater than 99% and flux remained constant at 100 GFD for the duration. The same solution circulated through a flat sheet test unit with the same membrane resulted in rejections of 43% for bovine serum albumin, 41% for beta-lactoglobulin and 31% for alpha-lactalbumin after only 5 minutes.

Example 2

20 L of whey protein isolate solution (20% W/V) in distilled water was recirculated through a microfiltration unit equipped with a static membrane with a rotating disk in close proximity to its surface. (DMF test unit, Pall Corporation) A 0.1 micron Nylon 66 membrane (Pall Corporation) was used. Temperatures ranged from 25° C. to 50° C. over an 8 hour run. In all cases testing showed the concentration of protein in the permeate to be identical to that of the feed while bacteria removal was greater than 99%.

Conclusion

Thus, by the present invention, a process is provided which is particularly effective with whey protein solutions and may be used for the removal of bacteria or lipids or for the fractionation of individual proteins.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. In a process for the membrane filtration of a protein solution, the improvement of: applying a high shear force at the surface of said membrane, said high shear force being generated by relative rotation, at a speed of between about 1,000 to about 3,450 RPM, between a membrane disc and a solid disc which are spaced in close proximity to one another with a space therebetween of about ⅛" to about ¼".

2. The process of claim 1 wherein said membrane disc is stationary and said solid disc is rotating.

3. The process of claim 1 wherein said membrane disc is rotating and said solid disc is stationary.

4. The process of claim 1 where said protein solution is milk, whey, concentrated whey or a purified solution of whey proteins.

5. The process of claim 4 for the membrane filtration to reject at least one of immunoglobulin and bovine serum albumin, and to pass beta-lactoglobulin and alpha-lactalbumin into a permeate.

6. The process of claim 5 wherein said permeate is further concentrated to provide a concentrate and wherein said concentrate is dried to produce individual whey protein fractions.

7. The process of claim 5 wherein said permeate is subjected to at least one of further concentration and diafiltration steps to produce a whey protein isolate containing greater than about 90% protein on a dry basis.

8. The process of claim 4 for the membrane filtration to reject beta-lactoglobulin, and to pass alpha-lactalbumin into a permeate.

9. The process of claim 8 wherein said permeate is subjected to at least one of further concentration and diafiltration steps to produce a whey protein isolate containing greater than about 90% protein on a dry basis.

10. The process of claim 8, wherein said permeate is further concentrated to provide a concentrate and wherein said concentrate is dried to produce individual whey protein fractions.

11. The process of claim 1 wherein said membrane has a pore size which is selected to reject bacteria, but which is selected to allow substantially all protein to pass therethrough.

12. The process of claim 1 wherein said membrane has a pore size which is selected to reject lipid material, but which is selected to allow substantially all protein to pass therethrough.

* * * * *